United States Patent
Bicalho et al.

(10) Patent No.: US 12,310,937 B2
(45) Date of Patent: May 27, 2025

(54) FATTY ACID COMPOSITIONS

(71) Applicant: Fera Diagnostics and Biologicals Corp., College Station, TX (US)

(72) Inventors: Rodrigo Carvalho Bicalho, College Station, TX (US); Marjory Xavier Rodrigues, College Station, TX (US); Leonardo Bringhenti, College Station, TX (US)

(73) Assignee: Fera Diagnostics and Biologicals Corp., College Station, TX (US)

( * ) Notice: Subject to any disclaimer, the term of this patent is extended or adjusted under 35 U.S.C. 154(b) by 0 days.

(21) Appl. No.: 18/885,140

(22) Filed: Sep. 13, 2024

(65) Prior Publication Data

US 2025/0000833 A1  Jan. 2, 2025

Related U.S. Application Data

(63) Continuation of application No. PCT/US2022/051632, filed on Dec. 2, 2022.

(60) Provisional application No. 63/319,545, filed on Mar. 14, 2022.

(51) Int. Cl.
| | | |
|---|---|---|
| A61K 31/201 | (2006.01) |
| A61K 31/202 | (2006.01) |
| A61K 35/06 | (2006.01) |
| A61K 45/06 | (2006.01) |
| A61P 1/12 | (2006.01) |
| A61P 3/04 | (2006.01) |
| A61P 15/00 | (2006.01) |
| A61P 25/00 | (2006.01) |

(52) U.S. Cl.
CPC .......... *A61K 31/201* (2013.01); *A61K 31/202* (2013.01); *A61K 35/06* (2013.01); *A61K 45/06* (2013.01); *A61P 1/12* (2018.01); *A61P 3/04* (2018.01); *A61P 15/00* (2018.01); *A61P 25/00* (2018.01)

(58) Field of Classification Search
CPC .................................................... A61K 31/201
See application file for complete search history.

(56) References Cited

U.S. PATENT DOCUMENTS

| | | |
|---|---|---|
| 6,384,252 B1 | 5/2002 | Pageat |
| 8,957,115 B2 | 2/2015 | Nouvel et al. |
| 10,149,827 B2 | 12/2018 | Migliaccio et al. |
| 2011/0144141 A1 | 6/2011 | Hu et al. |
| 2016/0354292 A1 | 12/2016 | Obukowho et al. |
| 2017/0096418 A1 | 4/2017 | Patron et al. |
| 2017/0196793 A1 | 7/2017 | Wu |

OTHER PUBLICATIONS

International Search Report and Written Opinion, mailed Apr. 24, 2023 for International Application No. PCT/US2022/051632.
[No Author Listed], Minerals oils. L'Oreal. Nov. 18, 2020. Accessed from <https://web.archive.org/web/20201118205740/https://inside-our-products.loreal.com/ingredients/minerals-oils#:-:text=we%20use%20them%3F-,What%20are%20mineral%20oils%3F,are%20petrolatum%20and%20paraffin%20oil>. 8 pages.
PCT/US2022/051632, Apr. 24, 2023, International Search Report and Written Opinion.

*Primary Examiner* — Yong S. Chong

(74) *Attorney, Agent, or Firm* — Wolf, Greenfield & Sacks, P.C.

(57) ABSTRACT

A composition comprising a mixture of fatty acids such as linoleic, oleic, and palmitic acids or derivatives thereof derived from secretions of mammalian mammary glands. This composition can be utilized to decrease stress, anxiety, and aggressiveness in mammals.

24 Claims, 6 Drawing Sheets

FATTY ACID COMPOSITIONS

CROSS REFERENCE

This application claims priority under 35 U.S.C. §§ 120 and 365(c) to and is a continuation of International PCT Application No. PCT/US2022/051632, filed Dec. 2, 2022, which claims priority under 35 U.S.C. § 119(e) to U.S. Provisional Application, U.S. Ser. No. 63/319,545, filed Mar. 14, 2022, each of which is incorporated herein by reference.

FIELD OF THE INVENTION

The invention relates to a composition comprising a mixture of fatty acids or derivatives solubilized in a mineral oil. This composition is utilized to decrease the incidence of economically important diseases of farm animals.

BACKGROUND

Stress is the negative reaction of an animal's body to deleterious forces of nature, infections, and various abnormal states that tend to disturb homeostasis.

Animals exposed to stress respond with changes in the activity of the autonomic and neuroendocrine systems and in behavior. The activation of these biological systems is a prerequisite for the animal to cope with stress and thus is the principal resource that will provide the adequate biological defense against a threat that challenges the homeostasis of the animal.

In animals, including humans, stress stimulates the release of Adenocorticotropic hormone (ACTH), which controls the release of cortisol from the adrenal cortex.

In humans, stress can lead to medical problems such as ulcers, erosions, acute gastritis, and diarrhea. Onsets of erythrocytosis, inflammatory bowel disease, heart attacks, and ischemia are influenced by stress. There is a valid clinical impression that psychic or emotional stress and anxiety are associated with precipitation of overt ischemic heart diseases and sudden death.

Mammals such as pigs, dogs, cattle, and the like are also influenced by changes in their environment. The result of animals being taken out of their environment, being herded together, and transported often results in the animals being stressed. As a consequence, pathological disorders, mortality, delays in growth, and disorders in behavior often occur in stress-related conditions. Disorders in behavior often lead to aggressive fighting when animals are stressed.

Social stress is common during the growing period. This social stress often occurs as a consequence of separation from the dam, moving to a new environment, and mixing with unacquainted younglings.

This social stress often leads to antagonistic behavior among animals, which consists of fighting or trying to escape. For example, piglets begin fighting within hours of birth. When pigs of any age meet, a fight is likely to occur. It has been suggested that a pheromone is released during the end of a fight that signals submission.

For dairy cattle, the transition period is defined as the period from 21 days before to 21 days after parturition, and it is known to be an extremely important and challenging period of the life cycle of dairy cows. High-producing dairy cows undergo extreme metabolic adaptations during this period. Feed consumption increases approximately 2-fold between the week preceding parturition and the first 30 days postpartum; however, nutrient intake is often insufficient to meet lactation demands. As a result of this catabolic state, high-producing dairy cows might lose 1.5 kg/day of body weight in the first three weeks postpartum when energy balance is −7 to −9 Mcal net energy for lactation (NEL)/day. Additionally, the transition period presents a formidable collection of stressful events for dairy cows. Prepartum cows are transferred to individual calving pens during stage-1 of parturition. Their newborn calves are separated from their dams immediately after parturition. Postpartum cows are then moved to postpartum lactating cow pens, from which they are taken to milking parlors 3 times daily. For first lactation cows this will be their first exposure to the milking parlor and milking procedures. Therefore, the transition period exposes animals to incredible levels of social, nutritional, environmental, and physiological stresses which often leads to morbidity, mortality, and losses in productivity. Retained placenta, metritis, mastitis, and lameness are among the several diseases that plague postpartum dairy cows.

Retained fetal membranes (RFM) is defined as the failure to expel the placenta within 24 hours after calving. It has been hypothesized that RFM might be caused by an impaired immune function during the peripartum period, with a special emphasis on neutrophil function and migration. Thus, the failure of placental detachment seems to be, at least in part, due to a reduced ability of neutrophils to digest the cotyledon-caruncle attachment after parturition.

Metritis occurs within 21 days postpartum and is defined as an inflammatory process of the uterus characterized by fetid, red-brown, and watery uterine discharge associated with signs of systemic illness and rectal temperature (RT) >39.5° C. When systemic signs are not present and RT ≤39.5, the condition may be defined as clinical metritis. Metritis is associated with reduced milk production, poor reproductive performance, high treatment cost and increased risk of culling, resulting in significant economic losses.

Mastitis is a highly prevalent disease in dairy cows and arguably the most important disease for the dairy industry worldwide, causing economic losses due to reduced milk production, discarded milk, lower conception rates, premature culling, and treatment costs. The well-documented reduction in milk production resulting from mastitis is estimated at approximately 15% of the milk production potential of the affected cow. Clinical mastitis is also a serious animal welfare issue as it is associated with pain, reduced well-being, and behavioral changes.

Despite decades of research dedicated to advancing knowledge and aiding in the prevention of periparturient disorders (e.g., lameness, mastitis, retained placenta, and metritis) their incidences are still high. Moreover, these infectious diseases are frequently treated with systemic or local antibiotic therapy. The emergence of antibiotic-resistant bacteria is a mounting concern since many of the antibiotics used in animal agriculture can also be used in human medicine. Considering this, there is growing demand for a substitute to antibiotic use and for more effective treatment options that could improve health in dairy cows.

Diarrhea is one of the main causes of death and financial loss during the pre-weaning period of farmed mammals. It is also one of the most common (18.2%) diseases in pre-weaned heifers. Calves in the first month of life have the greatest risk of developing diarrhea. Furthermore, the occurrence of diarrhea in young calves has been found to be a predisposing factor to other diseases later in life, such as pneumonia. Diarrhea may occur as a result when a neonatal calf is exposed to various infectious or non-infectious risk factors. The most important risk factors in newborn calves are nutritional management, environmental condition, and pathogen exposure such as sanitation status. The most common entero-pathogens associated with diarrhea in the first month of calves' life are rotavirus, coronavirus, *E. coli, Cryptosporidium* spp., and coccidia.

Pageat (U.S. Pat. No. 6,169,113) (hereinafter "the '113 patent") discloses a pheromone composition (see Table 1) that can decrease stress, anxiety, and aggressiveness in mammals. The pheromone formulations that were claimed are "A process to reduce mortality and morbidity during infection in a mammal, said process comprising administering to a mammal in need of such treatment a solution comprising palmitic acid, oleic acid, linoleic acid and derivatives thereof as main active ingredients, wherein said solution comprises between about 18% to 31.2% (w %/w %) palmitic acid, about 34.3% to 47.2% (w %/w %) linoleic acid, about 28.7% to 42.8% (w %/w %) oleic acid and derivatives thereof," as set forth in Claim 2 of the '113 patent, and "A process to reduce mortality and morbidity during infection in a mammal, said process comprising administering to a mammal in need of such treatment a solution comprising palmitic acid, oleic acid, linoleic acid and derivatives thereof as main active ingredients, wherein said solution comprises between about 18% to 31.2% (w %/w %) palmitic acid, about 34.3% to 47.2% (w %/w %) linoleic acid, about 8.7% to 16% (w %/w %) palmitoleic acid, about 15.7% to 30.7% (w %/w %) oleic acid and derivatives thereto," as set forth in Claim 3 of the '113 patent.

The fatty acids (FA) were dissolved and homogenized in 94% propylene glycol and 6% absolute alcohol at 37.5° C. A study was disclosed to evaluate the pheromone effects on piglets. Piglets were grouped and tested using propylene glycol as a placebo and the pheromone formulation at a 5% concentration as treatment. In summary, it was reported that piglets receiving placebo were 86% more aggressive and stressed than piglets treated with the pheromone composition. Furthermore, the placebo group had a loss of weight compared to the treated group. However, no effects on disease prevention were reported.

TABLE 1

Formulation of the pheromone described in the '113 Patent

| Fatty acid | % |
| --- | --- |
| Linoleic acid | 35.2 |
| Palmitic acid | 20.5 |
| Palmitoleic acid | 11.2 |
| Oleic acid | 19.6 |
| Myristic acid | 6.2 |
| Lauric acid | 5.3 |
| Capric acid | 2 |
| Total | 100 |

SUMMARY OF THE INVENTION

Figure 1:
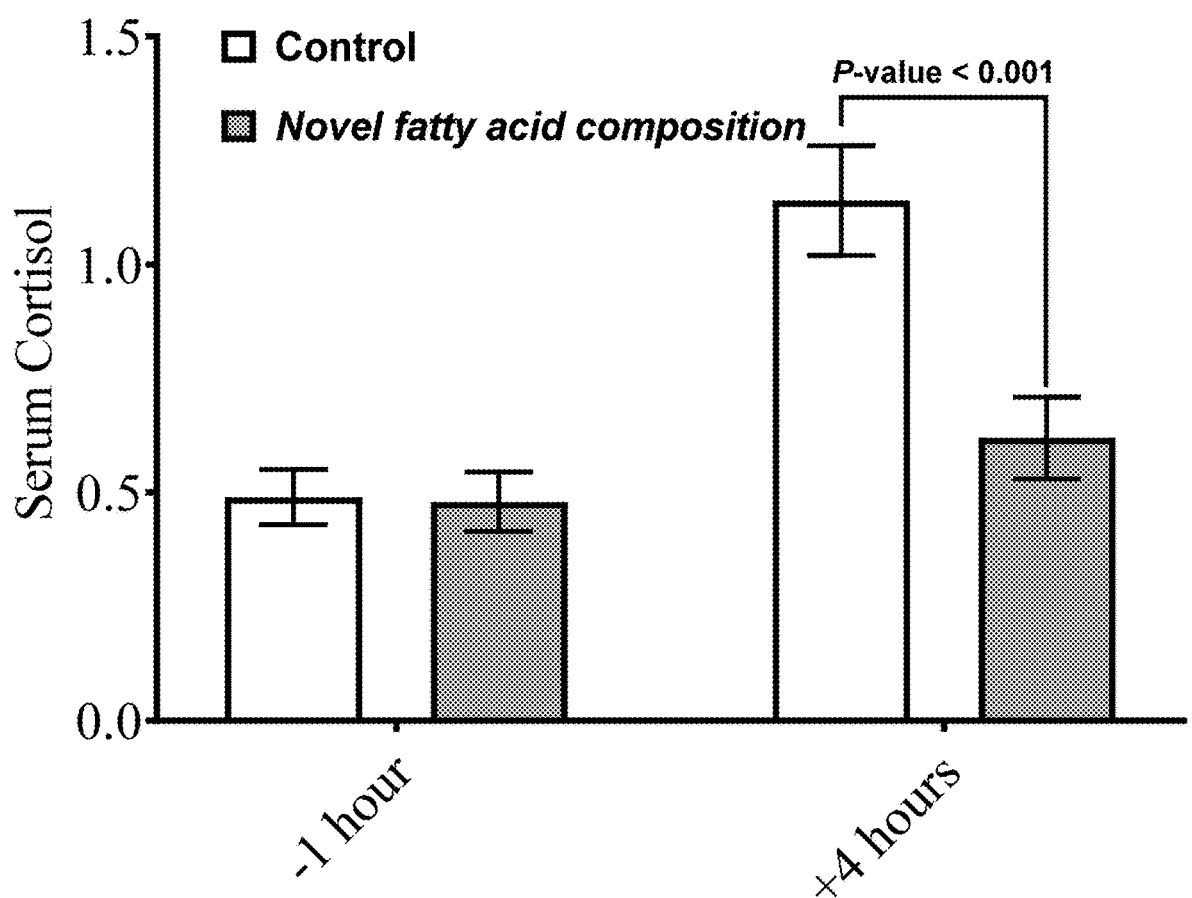
FIG. 1: shows the effect of treatment with the novel fatty acid composition on the levels of serum cortisol after castration.

It is an object of the invention to provide a treatment for the prevention or amelioration of economically important diseases of farm animals.

Another object of the invention is to provide a composition that enhances weight gain in mammals.

Another object of the invention is to reduce mortality and morbidity in mammals.

Another object of the invention is to reduce the incidence of retained placenta in mammals.

Another object of the invention is to reduce the incidence of metritis in mammals.

Another object of the invention is to reduce the incidence of lameness in mammals.

Another object of the invention is to reduce the incidence of mastitis in mammals.

Another object of the invention is to reduce feed conversion efficiency; i.e., the ratio of food consumed/weight gained.

Another object of the invention is to mitigate the pain experienced by a mammal that is exposed to a painful procedure (e. g., castration, dehorning, or accidental physical injury) comprising the step of administering to a mammal in need thereof a pharmaceutically effective amount of a composition of the invention.

Another object of the invention is to mitigate the stress experienced by a mammal that is exposed to a painful procedure (e. g., castration, dehorning or accidental physical injury) comprising the step of administering to a mammal in need thereof a pharmaceutically effective amount of a composition of the invention.

Another object of the invention is to increase the body weight gain of a mammal after experiencing a painful procedure (e. g.; castration, dehorning, or accidental physical injury) comprising the step of administering to a mammal in need thereof a pharmaceutically effective amount of a composition of the invention.

In one of the composition aspects, the invention provides a composition of 8 fatty acids dissolved in mineral oil.

In another composition aspect, the invention provides a basic fatty acid composition comprising palmitic acid, oleic acid, palmitoleic acid, linoleic acid, and derivatives thereof which composition also has the ability to reduce the incidence of diseases of farm animals.

In another composition aspect, the invention provides a composition comprising linoleic acid, palmitic acid, palmitoleic acid, oleic acid, arachidonic acid, myristic acid, lauric acid, capric acid, and derivatives thereof dissolved in mineral oil.

DETAILED DESCRIPTION OF THE INVENTION

In the present invention a new formulation of eight FAs is presented. The formulation comprises arachidonic acid, the main member of the ω-6 series. Its derivatives include endocannabinoids, which are oxidation-independent derivatives, critically significant for: brain reward signaling, motivational processes, emotion, stress responses, pain, and energy balance This fatty acid was not recited in the '113 patent nor in any other publication for this purpose. In addition, the proportions of FAs were redefined. The FAs of the inventive formulation are shown in Table 2.

Also of importance, the complete fatty acid formulation is effective in dramatically reducing the incidence of several economically important diseases such as diarrhea, retained placenta, metritis, mastitis, and lameness. Mortality rates are also reduced in animals treated with the novel fatty acid formulation. Reduction in pain and reduction in pain-related stress are also observed in mammals treated with the fatty acid formulation of the invention. These effects are novel and were not recited in the '113 patent nor in any other publication for this purpose.

TABLE 2

Novel fatty acids formulation for an appeasing pheromone composition

| Fatty acid | % |
| --- | --- |
| Linoleic acid | 30 |
| Palmitic acid | 16 |
| Oleic acid | 24 |
| Arachidonic acid | 8 |
| Myristic acid | 10 |
| Lauric acid | 8 |
| Capric acid | 3 |
| Behenic acid | 1 |
| Total | 100 |

Unlike propylene glycol, which is the solvent recited in the '113 patent, the solvent of the inventive composition is mineral oil. As used herein, the term "mineral oil" is any of various colorless, odorless, light mixtures of higher alkanes from a mineral source, particularly a distillate of petroleum. Mineral oil is widely used as a moisturizer to treat or prevent dry, rough, scaly, itchy skin and minor skin irritations, which is an important characteristic for this invention since the pheromone application is topical. Mineral oil is a colorless, transparent, oily liquid that is odorless and tasteless, and considered GRAS (Generally Regarded as Safe). Pharmaceutical-grade mineral oil, food-grade mineral oil, and/or industrial grade mineral oil are all liquid by-products of refining crude petroleum to make gasoline and other petroleum products. Mineral oil is a transparent, colorless oil, composed mainly of alkanes and cycloalkanes, related to petroleum jelly. It has a density of around 0.8-0.87 g/cm$^3$ (0.029-0.031 lb/cu in). All grades of mineral oil are useful in the inventive formulation.

One embodiment of the invention is a basic fatty acid composition comprising between about 0.5% to 42.8% (wt %/wt %) oleic acid, and derivatives thereof.

Another embodiment of the invention is a second basic fatty acid composition comprising between about 0.5% to 52.2% (wt %/wt %) myristic acid, and derivatives thereof.

Another embodiment of the invention is a third basic fatty acid composition comprising between about 0.5% to 42.8% (wt %/wt %) oleic acid and 0.5% to 52.2% (wt %/wt %) myristic acid, and derivatives thereof.

Another embodiment of the invention is a fourth basic fatty acid composition comprising between about 0.5% to 42.8% (wt %/wt %) oleic acid, 0.5% to 52.2% (wt %/wt %) myristic acid, 3% to 31.2% (wt %/wt %) palmitic acid, and derivatives thereof.

Another embodiment of the invention is a fifth basic fatty acid composition comprising between about 0.5% to 42.8% (wt %/wt %) oleic acid, 0.5% to 52.2% (wt %/wt %) myristic acid, 3% to 31.2% (wt %/wt %) palmitic acid, 0.5 to 25 (wt %/wt %) arachidonic acid, and derivatives thereof.

Another embodiment of the invention is a sixth basic fatty acid composition comprising between about 0.5% to 42.8% (wt %/wt %) oleic acid, 0.5% to 52.2% (wt %/wt %) myristic acid, 3% to 31.2% (wt %/wt %) palmitic acid, 0.5 to 25 (wt %/wt %) arachidonic acid, 0.2% to 12.5% (wt %/wt %) lauric acid, and derivatives thereof.

Another preferred embodiment of the invention is a fatty acid composition comprising between about 0.5% to 42.8% (wt %/wt %) oleic acid, 0.5% to 52.2% (wt %/wt %) myristic acid, 3% to 31.2% (wt %/wt %) palmitic acid, 0.5 to 25 (wt %/wt %) arachidonic acid, 0.2% to 12.5% (wt %/wt %) lauric acid, 0.1% to 22.6% (wt %/wt %) capric acid, and derivatives thereof.

Another preferred embodiment of the invention is a fatty acid composition comprising between about 0.5% to 42.8% (wt %/wt %) oleic acid, 0.5% to 52.2% (wt %/wt %) myristic acid, 3% to 31.2% (wt %/wt %) palmitic acid, 0.5 to 25 (wt %/wt %) arachidonic acid, 0.2% to 12.5% (wt %/wt %) lauric acid, 0.1% to 22.6% (wt %/wt %) capric acid, 8% to 65% (wt %/wt %) linoleic acid, and derivatives thereof.

Another preferred embodiment of the invention is a fatty acid composition comprising between about 0.5% to 42.8% (wt %/wt %) oleic acid, 0.5% to 52.2% (wt %/wt %) myristic acid, 3% to 31.2% (wt %/wt %) palmitic acid, 0.5 to 25 (wt %/wt %) arachidonic acid, 0.2% to 12.5% (wt %/wt %) lauric acid, 0.1% to 22.6% (wt %/wt %) capric acid, 8% to 65% (wt %/wt %) linoleic acid, 0.1% to 12.6% (wt %/wt %) behenic acid, and derivatives thereof.

Another embodiment of the invention is the fatty acid mixture dissolved in mineral oil at a concentration ranging from 1% to 35% (wt %/wt %). Homogenization is easily accomplished at concentrations as high as 35% by heating the mixture to 60° C. with vigorous agitation. Solutions are stable at concentrations as high as 35% with no saturation or saponification.

Another embodiment of the invention is a process to treat stress, anxiety, aggressive behavior, or weight loss in a mammal, said process comprising the step of administering to a mammal in need of such treatment a pharmaceutically effective amount of the composition of the invention.

Another embodiment of the invention is a process to reduce mortality and morbidity in a mammal, said process comprising the step of administering to a mammal in need of such treatment a pharmaceutically effective amount of the composition of the invention.

Another embodiment of the invention is a process to reduce the incidence of diarrhea in a mammal, said process comprising the step of administering to a mammal in need of such treatment a pharmaceutically effective amount of the composition of the invention.

Another embodiment of the invention is a process to reduce the incidence of retained placenta in a mammal, said process comprising the step of administering to a mammal in need of such treatment a pharmaceutically effective amount of the composition of the invention.

Another embodiment of the invention is a process to reduce the incidence of metritis in a mammal, said process comprising the step of administering to a mammal in need of such treatment a pharmaceutically effective amount of the composition of the invention.

Another embodiment of the invention is a process to reduce the incidence of mastitis in a mammal, said process comprising the step of administering to a mammal in need of such treatment a pharmaceutically effective amount of the composition of the invention.

Another embodiment of the invention is a process to reduce the incidence of lameness in a mammal, said process comprising the step of administering to a mammal in need of such treatment a pharmaceutically effective amount of the composition of the invention.

Another embodiment of the invention is a process to improve feed conversion in a mammal, said process comprising the step of administering to a mammal in need of such treatment a pharmaceutically effective amount of the composition of the invention.

Another embodiment of the invention is a process to reduce body weight shrinkage during transportation, said process comprising the step of administering to a mammal in need of such treatment a pharmaceutically effective amount of the composition of the invention.

Another embodiment of the invention is a process to increase hot carcass weight, said process comprising the step of administering to a mammal in need of such treatment a pharmaceutically effective amount of the composition of the invention.

Another embodiment of the invention is a process to mitigate the pain experienced by a mammal that is exposed to a painful procedure comprising the step of administering to a mammal in need of such treatment a pharmaceutically effective amount of a composition of the invention.

Another embodiment of the invention is a process to mitigate the stress experienced by a mammal that is exposed to a painful procedure comprising the step of administering to a mammal in need of such treatment a pharmaceutically effective amount of a composition of the invention.

Another embodiment of the invention is a process for increasing the body weight gain in a mammal that is exposed to a painful procedure comprising the step of administering to a mammal in need of such treatment a pharmaceutically effective amount of a composition of the invention.

As used herein, the word "mammal" encompasses any group of vertebrates the females of which have milk-secreting glands. The term "mammals" includes, but is not limited to, cats, humans, dogs, pigs, rats, mice, cattle, horses, apes, chimpanzees, dolphins, porpoises, orcas, and the like.

By "stress" is meant the reaction of an animal body to forces of deleterious nature, infections, and various abnormal states that tend to disturb homeostasis. This reaction may be a physical reaction or an emotional reaction such as anxiety.

By "anxiety" is meant an apprehension of anger and dread accompanied by restlessness, tension and the like, which is a reactional status characterized by a high probability of providing behavioral and emotional responses of fright. In neurophysical terms, this anxious state is accompanied by hyperactivity of the noradrenergic and serotonin systems.

By "antagonistic behavior" is meant aggressive or defensive social interaction between individuals of the same species such as fighting, fleeing, or submitting.

By "stress-associated diseases" is meant any disease whose symptoms increase due to stress.

By "reducing morbidity and mortality caused by infection" is meant that death and diseased states are reduced such that the mammal has a better chance of survival.

By "improved feed conversion efficiency" means the reduction of the ratio in food consumption/weight gained.

By the term "solution" is meant a liquid that has one or more compounds dispersed therein either by dissolution or suspension (e.g., a colloidal suspension).

By "appeasing effect" is meant a reduction of fear, apprehension, or anxiety, as well as the behavioral and physical consequences associated with stress. The behavioral consequences associated with stress include tremor, vocalization, flight, aggression, displacement activities, and the like. The physical consequences associated with stress include changes in heart rate, changes in levels of epinephrine, norepinephrine, ACTH, cortisol, glucose, and the like. In animals used as a source of food, this definition includes husbandry parameters such as growth weight and food conversion efficiency.

By "basic fatty acid composition" is meant a fatty acid composition that can be used cross-species in all mammals and comprises as the main active ingredients at least five fatty acids, which are oleic acid, myristic acid, palmitic acid, arachidonic acid, and lauric acid, and derivatives thereof. Optionally, the composition also contains 1-4 additional FAs, which are capric acid, palmitoleic acid, linoleic acid, behenic acid and derivatives thereof.

By "enhancer composition" is meant an active pheromonal composition that is species-specific and is used to enhance or act synergistically with the basic pheromonal composition to increase effectiveness in specific species of the basic composition.

More specifically, the basic composition of the invention comprises a mixture of at least five fatty acids (namely, oleic acid, myristic acid, palmitic acid, arachidonic acid, and lauric acid) and derivatives thereof which represent between about 15% to 95% (wt %/wt %) of the total composition, the remaining ingredients being mineral oil and, optionally, other non-toxic filler compounds, such as fatty acids, alcohols, amines, squalene and glycerol (more particularly, caproic acid, azelaic acid, propionic acid, geraniol, octadecatrianol, hexacosanol, trimethylamine, and methylamine.)

The basic composition can also be attached to a chemical carrier, provided that the bioactive structure of the fatty acids is preserved. Such carrier molecules include, but are not limited to resins, liposomes, crown compounds (e.g., macrocyclic polydentates), carrier proteins, and the like.

The fatty acids can be used in their pure form, i.e., as a free fatty acid, as well as their derivative form such as esters of fatty acids or salts of fatty acids, e.g., potassium laurate, potassium myristate, and potassium oleate.

The basic fatty acid composition can be diluted in various solutions, as set forth below and can also be used in various forms.

An enhancer composition containing between 5% to 35% (w %/w %) can also be added to the basic pheromonal composition, if desired. This enhancer composition comprises volatile organic compounds and mixtures thereof. This enhancer composition may be species-specific in nature and may vary according to the species selected for use of the invention.

The compounds that may be used in the enhancer composition, include, but are not limited to amines and fatty acids from indolic derivatives, esters of these amines and fatty acids, ketones such as acetone, alcohols, sterols and the like.

Besides the basic fatty acid composition and the enhancer composition, a preferred embodiment of the invention relates to a composition comprising free fatty acids, including decanoic acid, such as capric acid, dodecanoic acid, such as lauric acid, tetradecanoic acid, such as myristic acid, hexadecanoic acid, such as palmitic acid, cis-9-octadecanoic acid, such as oleic acid, linoleic acid and palmitoleic acid. Derivatives of these fatty acids can also be utilized in the invention. More specifically, these derivatives are esters of the fatty acids or salts of fatty acids.

The inventive composition may be in the form of a solution, aerosol spray, gel, slow-release matrix, shampoo, microencapsulation product, and the like. The solution can also be used as a topical treatment applied directly to the skin of animals. More specifically, the basic fatty acid composition can be applied as a topical pour-on solution to the skin of the animal.

The concentration of the above-mentioned fatty acids may vary depending upon the final form of use. However, the concentrations of the specific fatty acids that may be utilized and their concentration may be ascertained and tested according to the methods set forth herein. In Example 3, adult Holstein dairy cows received a 1,000 milligrams dose topically applied on the nuchal skin and the skin above the muzzle. The average live body weight of an adult Holstein dairy cow is 680 kg, hence; the dose administered to those animals in Example 3 was 1.47 milligrams per kilogram of live weight. In Example 4 newborn dairy calves were treated with a 1,000 milligrams dose topically applied on the nuchal skin and the skin above the muzzle. The average live body weight of a newborn Holstein calf is 45 kg. Therefore, in Example 4 Holstein dairy calves received a dose of 22.22 milligrams per kilogram of live body weight. In both examples the administration of the fatty acid concentration dramatically reduced the incidence of disease and mortality. Therefore, the effective dose of the above-mentioned fatty acid composition could vary from 0.1 mg/kg to 1,000 mg/kg.

Once obtained, the compositions of the invention can be tested for their efficacy to treat stress and diseases in mammals. Well documented stressors are, for example, extreme cooling, overcrowding, isolation, separation, confinement, proximity to predators, transportation, pain, and the like. Application of the present composition in the form of a spray, aerosol, and the like in an area surrounding the stressful events results in diminution of stress as indicated by a variety of factors such as weight gain, social behavior with respect to other mammals, wounds on the body, especially the ears, salivary cortisol, heart rate, and the like.

Thus, the present compositions can be applied to a variety of objects that the mammal comes in proximity to or in contact with, such as walls, air, and toys. The present compositions can also be applied to the skin, hair, or fur.

In order to further illustrate the invention, the following examples are given, it being understood that the same are intended only as illustrative and not limiting.

Example 1

Novel Fatty Acid Composition

The fatty acids used and their quantities are presented in Table 3. In total, eight different FAs were used. First, the four dry components were weighted and transferred to a 2-liter glass bottle; 16 grams of palmitic acid, 10 grams of myristic acid, 8 grams of lauric acid, 1 gram of behenic acid. Then, the four liquid FAs were aliquoted using graduated pipettes and dispensed into the same container; 30 mL linoleic acid, 24 mL of oleic acid, 8 mL of arachidonic acid, and 3 mL of capric acid. To the bottle containing the FA mixture was added 900 mL of mineral oil and the mixture was heated to 60° C. The final solution contained a 10% concentration of the final fatty acid mixture and 90% mineral oil. The solution was vigorously homogenized at 60° C. until complete dissolution of the crystals. Once, a homogenized solution was obtained, the bottle was placed at room temperature to cool down. The final product obtained was bottled in 30 mL glass vials and sealed for long term storage at room temperature. Bottles were identified with batch number, date, and composition. Several batches were performed as above described to verify the product's characteristics and stability. Visual examination of the bottles was regularly performed and revealed no changes in the product. The product was stable, homogenous, and colorless.

TABLE 3

Novel appeasing pheromone formulation

| Fatty acid | Quantity |
|---|---|
| Linoleic acid | 30 ml |
| Palmitic acid | 16 g |
| Oleic acid | 24 ml |
| Arachidonic acid | 8 ml |
| Myristic acid | 10 g |
| Lauric acid | 8 g |
| Capric acid | 3 g |
| Behenic acid | 1 g |
| Mineral Oil-USP Grade | 900 mL |
| Final Product | 1,000 mL |

Example 2

Composition Comparison

Two fatty acid compositions were prepared. The compositions were used to compare the formulation described in the Table 3 using mineral oil as solvent vs. one using 94% propylene glycol and 6% ethanol (as recited in the '113 patent) as solvent. The fatty acid concentration of the compositions was 20% wt/wt.

Mineral oil and 94% propylene glycol and 6% ethanol were heated to 60° C. All FAs were weighted and transferred to bottles to make a 500 mL composition with 20% of FA. After heating, each solvent was added to a respective bottle. The compositions were heated and homogenized until complete FA dissolution. The 20% FA mixtures were used to make compositions with 1%, 5%, and 10% of FA. Solvents were heated for proper dilution and homogenization. All flasks were well sealed followed by storage at room temperature.

Visual inspections of the compositions were made 24 hr and 72 hr post-preparation. The experiment and visual inspections were repeated several times to verify consistency of solution solubility and stability.

Compositions prepared with propylene glycol and ethanol were opaque and whitish while compositions prepared with mineral oil were colorless and translucent. After 24 hr, all compositions prepared with propylene glycol and ethanol were visually heterogeneous, opaque whitish with a top oil layer. On the other hand, mineral oil compositions were stable, colorless, translucent, and homogenous. Visually the fatty acid composition solubility in mineral oil is substantially superior. After 72 hr, the compositions prepared with propylene glycol and ethanol containing 10% and 20% of FA has visual precipitation and clumps of FA on the surface.

Absorbance (Abs) measurements were collected to better demonstrate the difference between the solvents and FA concentrations. The mineral oil compositions presented practically the same Abs independent of FA concentration. However, 94% propylene glycol and 6% ethanol compositions gradually increased Abs measurements according to FA concentrations. Using 1% of FA, the mineral oil composition presented Abs of 0.042 while propylene glycol and ethanol had Abs of 0.197. When 20% FA solutions were measured, the Abs of 0.059 and 1.385 were detected for mineral oil and propylene glycol and ethanol, respectively.

Example 3

Cow Testing

A study was conducted in a dairy farm on Holstein cows. All cows were offered a TMR (total mixed ratio) and feed was pushed up 8 times a day. Diets consisted of approximately 55% forage and 45% concentrate on a dry matter basis. Diets were formulated to meet or exceed the National Research Council nutrient requirements for lactating Holstein cows weighing 650 kg and producing 45 kg of 3.5% fat-corrected milk (National Research Council, 2001). Cows displaying signs of calving were moved to individual maternity pens for delivery. After calving, cows were transferred to a postpartum pen where they remained for approximately 40 days.

In total, 107 cows were enrolled in the study. Cows were blocked by parity (first parturition and second or greater parturition) and, within block, randomly allocated into one of two treatment groups: control group (CTR; n=53) and treated group (TRT; n=54). Cows were eligible to receive their respective treatments after they were detected displaying signs of calving and were moved to individual maternity pens for delivery. At the maternity pens the cows allocated to the control group did not receive any treatment and cows allocated to the treatment group receive the following topical application of the novel fatty acid formulation: 5 mL applied to the nuchal skin and 5 mL applied to the skin above the muzzle. The fatty acid composition (10% fatty acid mix and 90% mineral oil) was produced as detailed in Example 1.

Retained fetal membranes was defined as failure to deliver fetal membranes by 24 hr after calving. Metritis was diagnosed daily. Cows were flagged for a physical examination when showing signs of dullness and depression or when a milk deviation of more than 4.5 kg was detected. At the physical examination, cows were considered as metritis when a fetid, watery and red-brown uterine discharge combined with systemic illness was observed. Mastitis and lameness were also diagnosed by trained farm employees.

Cows that were treated with the fatty acid formulation of the invention had:
  Lower incidence of retained placenta (CTR=5.66% vs. TRT=1.84%)
  Lower incidence of metritis (CTR=15.1% vs. TRT=3.7%)
  Lower incidence of lameness (CTR=7.6% vs. TRT=3.7%)
  Lower incidence of mastitis (CTR=7.6% vs. TRT=5.6%).

Example 4

Dairy Calf Testing

The objective of this study was to evaluate the effect of an appeasing pheromone composition of the invention administrated at the first day of life and every 15 days thereafter on the incidence of diarrhea and mortality risk of Holstein dairy calves.

The study was conducted in a dairy farm. Immediately after parturition, calves were separated from their mothers and placed into a newborn pen bedded with dry wood shavings and heated with heating lamps during months with cold temperatures. All calves were fed approximately 4 L of pasteurized pooled colostrum within 5 hours of birth by an esophageal feeder (Oral Calf Feeder Bag with Probe, Jorvet). Once a day, calves were removed from the newborn pen and transported to the calf raising facilities and placed in individual calf hutches. Calves were fed milk twice daily and after the first week of life, solid feed started to be offered. The weaning process started at 50 days of calves' life by reducing the amount of milk offered until the complete absence of milk at 60 days of life. After weaning, calves were maintained in the hutches for approximately two weeks and then moved to collective pens comingling 20 calves per pen.

The experimental design was a complete randomized design. A total of 420 Holstein dairy calves were randomly enrolled in one of the two treatment groups (Treatment, N=210; Control, N=210). Calves in the treatment group received as the first treatment of the topical novel fatty acid formulation of the invention (Example 1, Table 3) a single dose containing (10 mL) of the novel fatty acid composition of the invention on their first day of life as soon as they were allocated in the calf hutches and then every 14 days until weaning. The treatment was applied through a topical administration to the nuchal skin (5 mL) and the skin above the muzzle (5 mL). Calves allocated in the control group did not receive any kind of treatment. The novel fatty acid composition (10% fatty acid mix and 90% mineral oil) was produced as detailed in (Example 1, Table 3). All enrolled calves were evaluated daily for a follow up period of 60 days.

Statistical analyses were performed. To analyze the effect of treatment on the binary response variables of the incidence of diarrhea and mortality risk, logistic regression was performed. Fisher's exact significance test was used considering the alternative hypothesis that the probability of diarrhea would be greater in the control group compared to the treatment group.

Treatment reduced the incidence of diarrhea and mortality risk during the pre-weaning period of the calves. The administration of the novel fatty acid formulation significantly reduced the incidence of diarrhea ($P<0.009$), which was diagnosed in 70.8% of calves assigned to the control group and in 58.6% of calves to the treatment group.

Mortality risk in the 60 days of life was statistically higher ($P=0.02$) for the control group (7.8%) compared to the treatment group (2.4%).

Example 5

Beef Calf Testing

To evaluate the effect of administering the novel fatty acid formulation on the prevention of body weight shrinkage following transportation two studies were performed. The novel fatty acid composition (10% fatty acid mix and 90% mineral oil) was produced as detailed in Example 1, Table 3. In studies 1 and 2, the novel fatty acid composition was administered to weaned beef calves prior to transportation from the sale barn to the feedlot for the evaluation of body weight loss ("shrinkage") during transportation.

Study 1—The experiment was conducted with calves transported from a receiving pen to a sale barn. A total of 38 calves with average body weight of 272 kg were used in the study. Calves were randomly allocated to be either in a treatment group (TRT, n=19) or a control group (CTR, n=19). Animals in the treatment group received a topical application of the novel fatty acid composition. Treatments were applied within 1 hour before loading in the trailer. A total dose of 10 mL was topically applied to the nuchal skin (5 mL) and the skin above the muzzle (5 mL). Control animals did not receive any treatments and were loaded into a different trailer to avoid contact with the treatment group. The transportation time of the animals from one facility to the other was approximately 5 hours. The group weights were measured prior to transportation and upon arrival at the final destination.

After the transportation of approximately 5 hours, calves in the control group lost a total of 415.5 kg (8%), while treated calves lost only a total of 71.2 kg (1.3%). Therefore, the use of the novel fatty acid formulation prevented 83.75% of the body weight shrinkage that was observed in the non-treated group.

Study 2—the experiment was conducted with calves transported from a sale barn to a feedlot yard. The transportation time of the animals from the sale barn to the feedlot was 12.5 hours. A total of 88 beef calves with average body weight of 250 kg were used in the study. Calves were randomly allocated to be either in a treatment group (TRT, n=19) or a control group (CTR, n=19). Animals in the treatment group received a topical application of the novel fatty acid composition with a total dose of 10 mL topically applied to the nuchal skin (5 mL) and the skin above the muzzle (5 mL). The novel fatty acid composition (10% fatty acid mix and 90% mineral oil) was produced as detailed in Example 1, Table 3. Treatments were applied within 1 hour before loading in the trailer. Control animals did not receive any treatments and were loaded into a different trailer to avoid contact with the treatment group. The group weights were measured prior to transportation and upon arrival at the final destination.

After the transportation of 12.5 hours, calves in the control group lost a total of 902.6 kg (7.55%), while calves in the treatment group lost a total of 13.6 kg (0.11%). Therefore, the use of the novel fatty acid formulation prevented 98.54% of the body weight shrinkage that was observed in the non-treated group.

Example 5

Finished Beef Cattle Testing

The experiment was conducted with fat beef cattle (finished beef cattle) transported from a feedlot to a slaughterhouse. A total of 76 beef steers with average live weight of 583 kg were used in the study. Steers were randomly allocated to be either in a treatment group (TRT, n=38) or a control group (CTR, n=38). Animals in the treatment group received a topical application of the novel fatty acid composition. Treatments were applied within 12 hours before loading in the trailer. A total dose of 10 mL was topically applied to the nuchal skin (5 mL) and the skin above the muzzle (5 mL). Control animals did not receive any treatments and were loaded into a different trailer to avoid contact with the treatment group. The novel fatty acid composition (10% fatty acid mix and 90% mineral oil) was produced as detailed in Example 1, Table 3. The transportation time of the animals from the feedlot to the slaughterhouse was approximately 5 hours. The individual live weights were recorded prior to transportation and hot carcass weights (HCW) were recorded at the slaughterhouse.

Study steers had an average live weight prior to transportation of 586.4 kg in the control group and 581.5 kg in the treatment group (p-value=0.89). After slaughter, the average hot carcass weight was significantly higher in the treatment group in comparison to the control group (treatment=352.5 kg±1.4; control=347.5 kg±1.4; P=0.01).

Example 6

Castrated Bulls

This experiment was conducted with 21-day old crossbred bull calves (Holstein crossed with Angus) in a calf ranch. A total of 33 bull calves were randomly allocated as control calves and 42 calves were allocated to receive the novel fatty acid treatment. Calves that were allocated to the novel fatty acid treatment received a total dose of 10 mL that was topically applied to the nuchal skin (5 mL) and the skin above the muzzle (5 mL). Treatment was applied 1 hour before animals were surgically castrated. Control animals did not receive any treatments and were housed separately to avoid contact with the treatment group. The novel fatty acid composition (10% fatty acid mix and 90% mineral oil) was produced as detailed in Example 1, Table 3. One hour after calves in the treatment group were treated with the novel fatty acid composition all calves were surgically castrated by a licensed veterinarian. To quantify stress and pain experienced by the research animals a blood sample was collected 1 hour prior to castration (baseline sample) and a second blood sample was collected 4 hours after the castration was performed. Blood samples were refrigerated immediately after collection and centrifuged. Serum was harvested and preserved in −80° C. freezers until the ELISA assays were performed. The quantification of Substance P was determined by Substance P ELISA Kit (ADI-900-018A, Enzo Life Science, Inc.). All serum samples were diluted to 1:150 with assay buffer immediately before use. Reagent preparation and assay procedure were performed according to manufacturer's instructions. Cortisol was also measured by an enzyme immunoassay kit; serum samples were 10-fold diluted with assay diluent provided in the kit Salivary Cortisol (1-3002, Salimetrics LLC). Procedures were followed in accordance with manufacturer's instructions.

Figure 2:
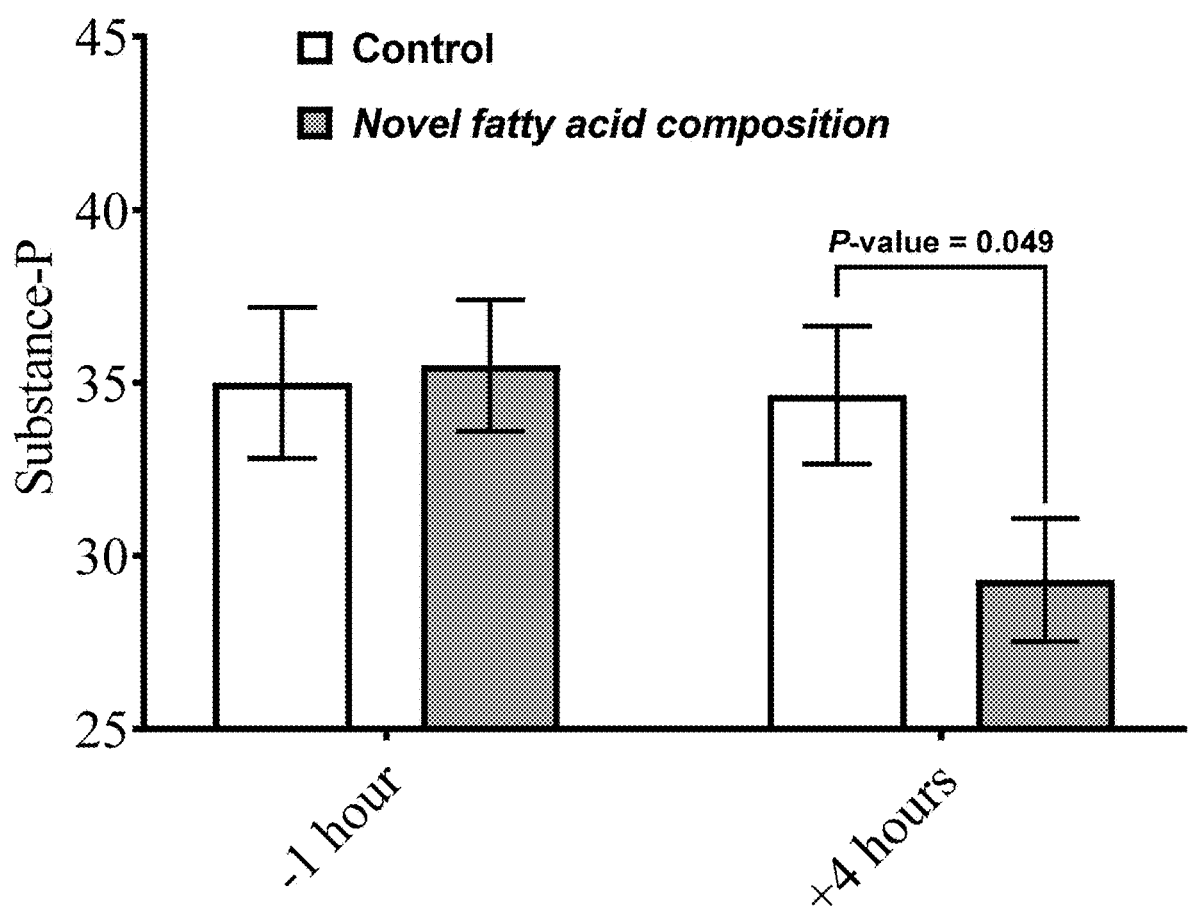
FIG. 2: shows the effect of treatment with the novel fatty acid composition on the levels of serum Substance-P after castration.
Figure 3:
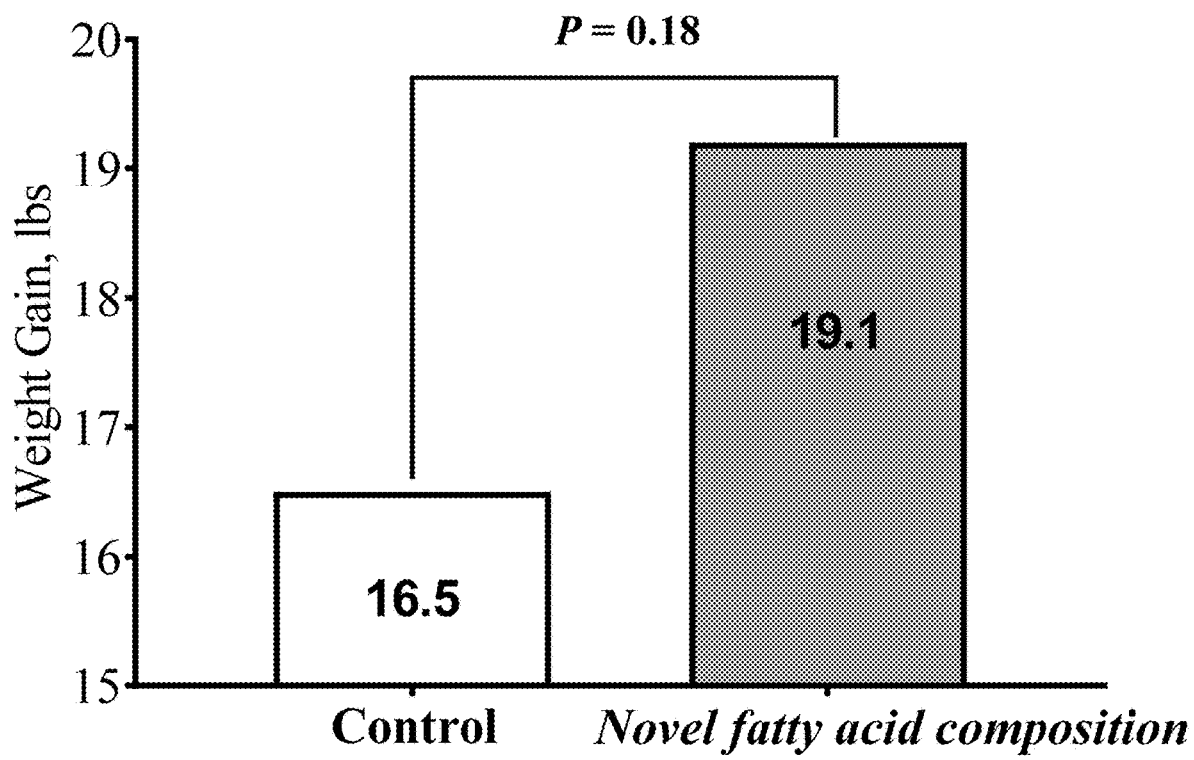
FIG. 3: shows the effect of treatment with the novel fatty acid composition on body weight gain after castration.

Animals that received the novel fatty acid composition treatment had significantly lower levels of stress associated with the castration procedure, which was evidenced by the significantly lower levels of cortisol 4 hours after castration (FIG. 1). Additionally, animals that received the novel fatty acid composition treatment experienced lower levels of pain, as evidenced by the significantly lower levels of Substance-P 4 hours after castration (FIG. 2). Furthermore, treatment with the novel fatty acid mixture increased weight gain 17-days after castration (FIG. 3).

Example 7

Dehorned Calves

This experiment was conducted with 21-day old Holstein dairy calves in a calf ranch. A total of 37 bull calves were randomly allocated as control calves and 32 calves were allocated to receive the novel fatty acid treatment. Calves that were allocated to the novel fatty acid treatment received a total dose of 10 mL that was topically applied to the nuchal skin (5 mL) and the skin above the muzzle (5 mL). Treatment was applied 1 hour before animals were surgically dehorned. Control animals did not receive any treatments and were housed separately to avoid contact with the treatment group. The novel fatty acid composition (10% fatty acid mix and 90% mineral oil) was produced as detailed in (Example 1, Table 3). One hour after calves in the treatment group were treated with the novel fatty acid composition all calves were surgically dehorned by a licensed veterinarian. To quantify stress and pain experienced by the research animals a blood sample was collected 1 hour prior to dehorning (baseline sample) and a second blood sample was collected 4 hours after the dehorning was performed. Blood samples were refrigerated immediately after collection and centrifuged, serum was harvested and preserved in −80° C. freezers until the ELISA assays were performed. The quantification of Substance P was determined by Substance P ELISA Kit (ADI-900-018A, Enzo Life Science, Inc.). All serum samples were diluted to 1:150 with assay buffer immediately before use. Reagent preparation and assay procedures were performed according to manufacturer's instructions. Cortisol was also measured by an enzyme immunoassay kit. Serum samples were 10-fold diluted with assay diluent provided in the kit Salivary Cortisol (1-3002, Salimetrics LLC). Procedures were followed in accordance with manufacturer's instructions.

Figure 4:
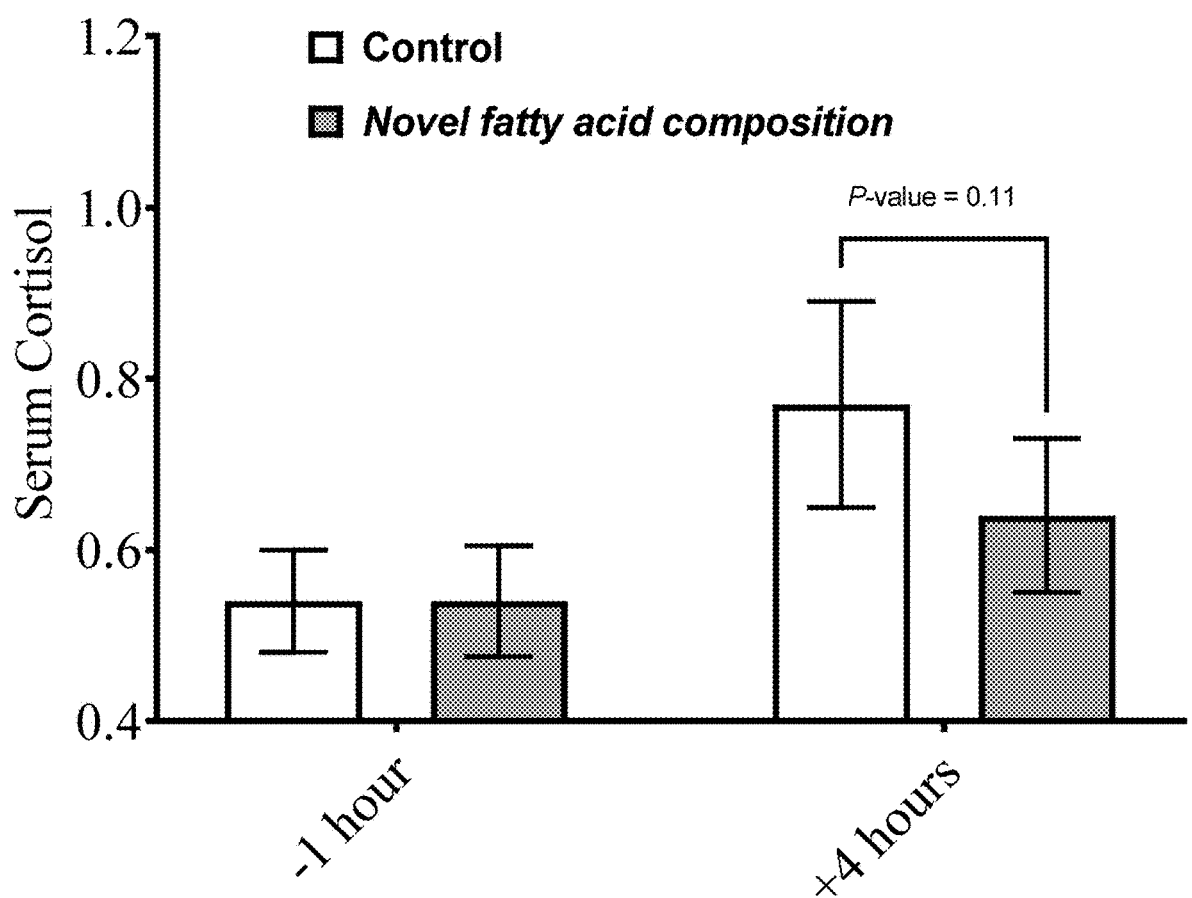
FIG. 4: shows the effect of treatment with the novel fatty acid composition on the levels of serum cortisol after dehorning.
Figure 5:
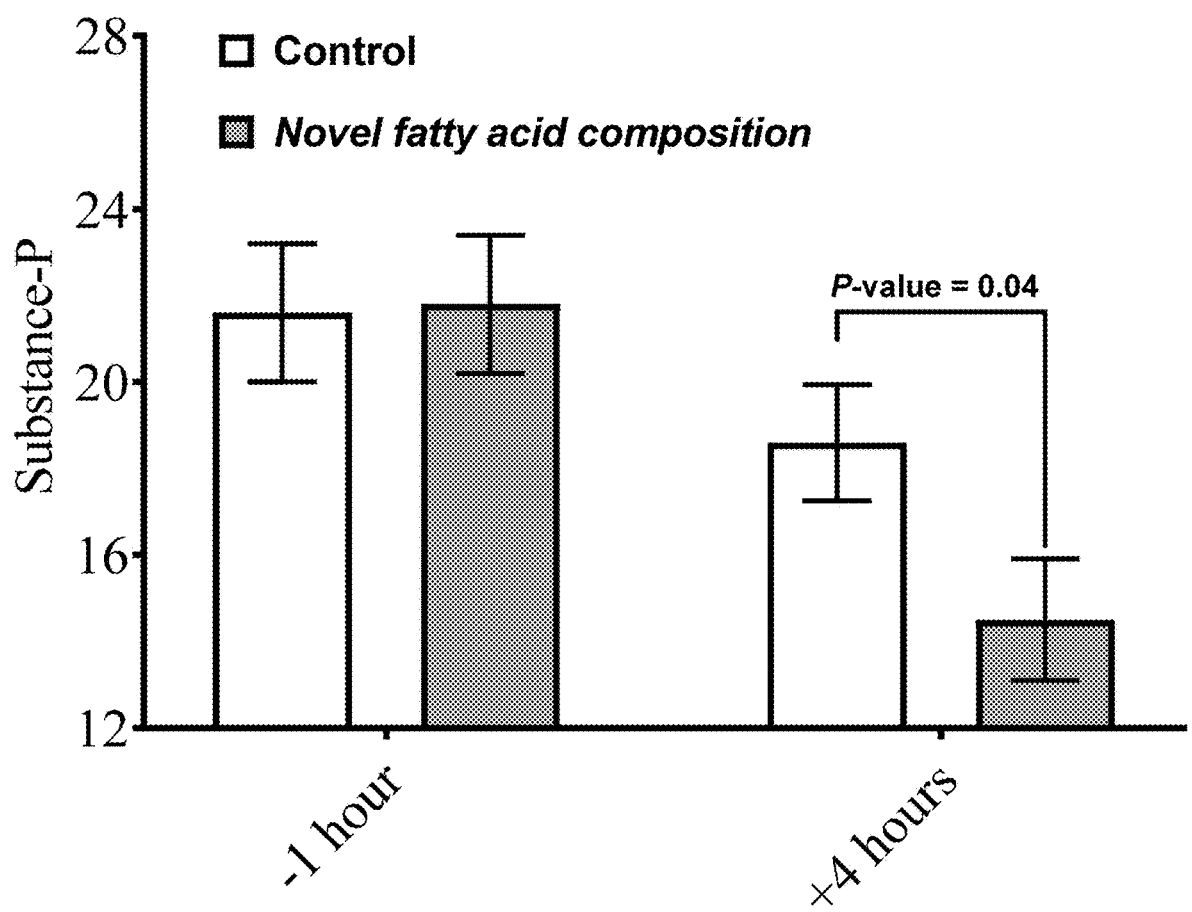
FIG. 5: shows the effect of treatment with the novel fatty acid composition on the levels of serum Substance-P after dehorning.
Figure 6:
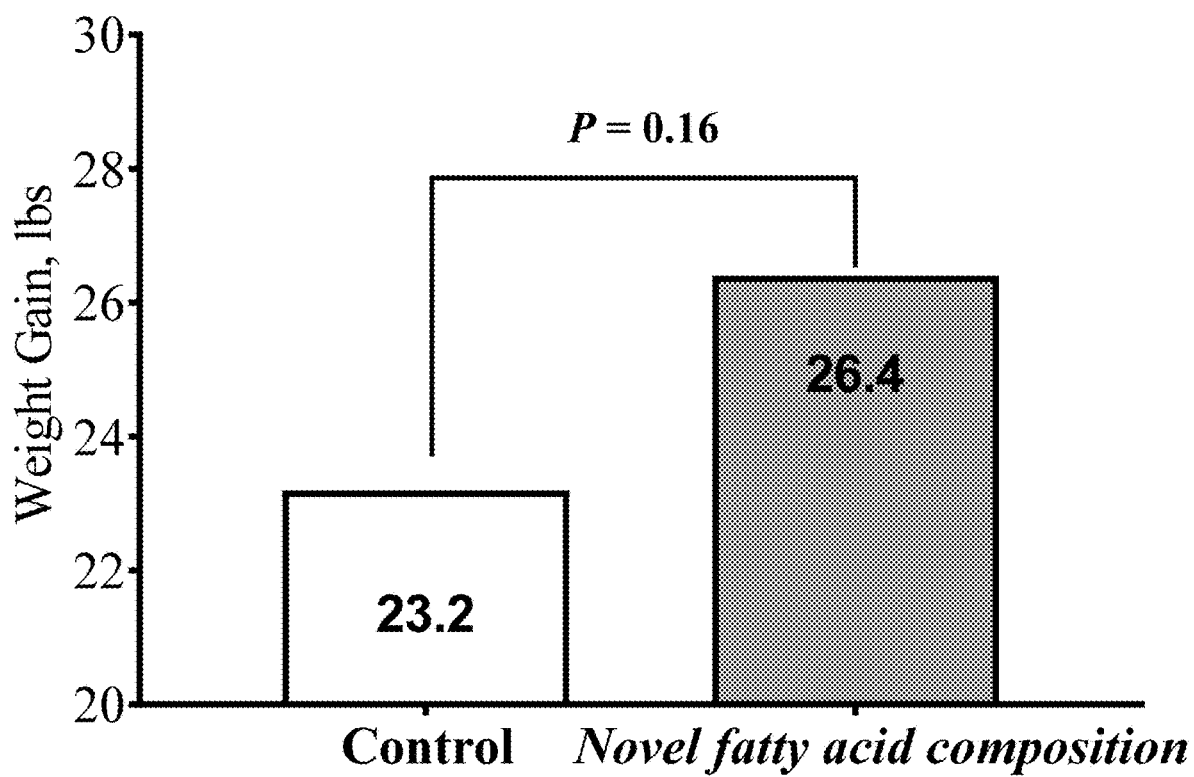
FIG. 6: shows the effect of treatment with the novel fatty acid composition on body weight gain after dehorning.

Animals that received the novel fatty acid composition treatment had significantly lower levels of stress associated with the dehorning procedure, which was evidenced by the significantly lower levels of cortisol 4 hours after dehorning (FIG. 4). Additionally, animals that received the novel fatty acid composition treatment experienced lower levels of pain, as evidenced by the significantly lower levels of Substance-P 4 hours after dehorning (FIG. 5). Furthermore, treatment with the novel fatty acid mixture increased weight gain 17-days after dehorning (FIG. 6).

What is claimed is:

1. A homogeneous solution consisting of mineral oil and a fatty acid composition, the fatty acid composition consisting of about 0.5-42.8% (wt/wt %) oleic acid, about 0.5-52.2% (wt/wt %) myristic acid, about 3-31.2% (wt/wt %) palmitic acid, about 0.5-25% (wt/wt %) arachidonic acid, about 0.2-12.5% (wt/wt %) lauric acid, about 0.1-22.6% (wt/wt %) capric acid, about 8-65% (wt/wt %) linoleic acid, and about 0.1-12.6% (wt/wt %) behenic acid, or derivatives thereof.

2. The homogeneous solution of claim 1, wherein the oleic acid is present in the fatty acid composition in an amount of about 24% (wt/wt %).

3. The homogeneous solution of claim 1, wherein the oleic acid is present in the fatty acid composition in an amount of about 22.8% (wt/wt %).

4. The homogeneous solution of claim 1, wherein the myristic acid is present in the fatty acid composition in an amount of about 10% (wt/wt %).

5. The homogeneous solution of claim 1, wherein the myristic acid is present in the fatty acid composition in an amount of about 10.7% (wt/wt %).

6. The homogeneous solution of claim 1, wherein the palmitic acid is present in the fatty acid composition in an amount of about 16% (wt/wt %).

7. The homogeneous solution of claim 1, wherein the palmitic acid is present in the fatty acid composition in an amount of about 17% (wt/wt %).

8. The homogeneous solution of claim 1, wherein the arachidonic acid is present in the fatty acid composition in an amount of about 8% (wt/wt %).

9. The homogeneous solution of claim 1, wherein the arachidonic acid is present in the fatty acid composition in an amount of about 7.9% (wt/wt %).

10. The homogeneous solution of claim 1, wherein the lauric acid is present in the fatty acid composition in an amount of about 8% (wt/wt %).

11. The homogeneous solution of claim 1, wherein the lauric acid is present in the fatty acid composition in an amount of about 8.5% (wt/wt %).

12. The homogeneous solution of claim 1, wherein the capric acid is present in the fatty acid composition in an amount of about 3% (wt/wt %).

13. The homogeneous solution of claim 1, wherein the capric acid is present in the fatty acid composition in an amount of about 3.2% (wt/wt %).

14. The homogeneous solution of claim 1, wherein the linoleic acid is present in the fatty acid composition in an amount of about 30% (wt/wt %).

15. The homogeneous solution of claim 1, wherein the linoleic acid is present in the fatty acid composition in an amount of about 28.8% (wt/wt %).

16. The homogeneous solution of claim 1, wherein the behenic acid is present in the fatty acid composition in an amount of about 1% (wt/wt %).

17. The homogeneous solution of claim 1, wherein the behenic acid is present in the fatty acid composition in an amount of about 1.1% (wt/wt %).

18. The homogeneous solution of claim 1, the fatty acid composition consisting of about 24% (wt/wt %) oleic acid, about 10% (wt/wt %) myristic acid, about 16% (wt/wt %) palmitic acid, about 8% (wt/wt %) arachidonic acid, about 8% (wt/wt %) lauric acid, about 3% (wt/wt %) capric acid, about 30% (wt/wt %) linoleic acid, and about 1% (wt/wt %) behenic acid, or derivatives thereof.

19. The homogeneous solution of claim 1, the fatty acid composition consisting of about 22.8% (wt/wt %) oleic acid, about 10.7% (wt/wt %) myristic acid, about 17% (wt/wt %) palmitic acid, about 7.9% (wt/wt %) arachidonic acid, about 8.5% (wt/wt %) lauric acid, about 3.2% (wt/wt %) capric acid, about 28.8% (wt/wt %) linoleic acid, and about 1.1% (wt/wt %) behenic acid, or derivatives thereof.

20. The homogeneous solution of claim 1, wherein the mineral oil is USP-Grade mineral oil.

21. The homogeneous solution of claim 1, consisting of about 65-99% (wt/wt %) mineral oil and about 1-35% (wt/wt %) the fatty acid composition.

22. The homogeneous solution of claim 1, consisting of about 90% (wt/wt %) mineral oil and about 10% (wt/wt %) the fatty acid composition.

23. The homogeneous solution of claim 1, consisting of about 88.5-89.3% (wt/wt %) mineral oil and about 10.7-11.5% (wt/wt %) the fatty acid composition.

24. The homogeneous solution of claim 1 prepared by dissolving the fatty acid composition in the mineral oil.

* * * * *